United States Patent
Shadduck

(10) Patent No.: US 8,992,609 B2
(45) Date of Patent: *Mar. 31, 2015

(54) INTRAOCULAR LENS SYSTEM AND METHOD FOR POWER ADJUSTMENT

(75) Inventor: John H. Shadduck, Menlo Park, CA (US)

(73) Assignee: PowerVision, Inc., Belmont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/852,733

(22) Filed: Aug. 9, 2010

(65) Prior Publication Data

US 2010/0324671 A1    Dec. 23, 2010

Related U.S. Application Data

(63) Continuation of application No. 11/069,136, filed on Feb. 28, 2005, now Pat. No. 7,776,088, which is a continuation of application No. 10/231,433, filed on Aug. 29, 2002, now abandoned.

(60) Provisional application No. 60/316,203, filed on Aug. 31, 2001.

(51) Int. Cl.
*A61F 2/16* (2006.01)

(52) U.S. Cl.
CPC .............. *A61F 2/1613* (2013.01); *A61F 2/1635* (2013.01)
USPC .......................... 623/6.13; 623/6.22; 623/6.34

(58) Field of Classification Search
CPC ............................. A61F 2/1635; A61F 2/1656
USPC ................................................ 623/6.13, 6.22
See application file for complete search history.

(56) References Cited

U.S. PATENT DOCUMENTS

| | | |
|---|---|---|
| 4,111,995 A | 9/1978 | Nelson |
| 4,251,887 A | 2/1981 | Anis |
| 4,253,199 A | 3/1981 | Banko |
| 4,254,509 A | 3/1981 | Tennant |
| 4,304,895 A | 12/1981 | Loshaek |

(Continued)

FOREIGN PATENT DOCUMENTS

| | | |
|---|---|---|
| EP | 0898972 A2 | 3/1999 |
| FR | 2784575 | 4/2000 |

(Continued)

OTHER PUBLICATIONS

Conlisk, A. T. et al; Mass Transfer and Flow in Electrically Charged Micro-and Nano-channels; Analytical Chemistry, vol. 74; iss. 9; pp. 2139-2150; 2002.

(Continued)

*Primary Examiner* — David H Willse
(74) *Attorney, Agent, or Firm* — Shay Glenn LLP

(57) ABSTRACT

An intraocular lens (IOL) that provides for optical power adjustment following its implantation, for example, for use in treating cataract patients. The lens body has first and second surface portions that bound at least one interior chamber or space that extends from the central optic portion to the lens periphery. The interior chamber or space has a microporous body that is intermediate inner and outer portions of the space. In one embodiment, the microporous body is capable of cooperating with an external Rf or light source to expose a charge to a charge-carrying fluid within the interior chamber. By this system, fluid flows are induced to alter the optical parameters of the lens.

24 Claims, 8 Drawing Sheets

(56) References Cited

U.S. PATENT DOCUMENTS

| | | |
|---|---|---|
| 4,373,218 A | 2/1983 | Schachar |
| 4,409,691 A | 10/1983 | Levy |
| 4,423,809 A | 1/1984 | Mazzocco |
| 4,435,856 A | 3/1984 | L'Esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | McClure |
| 4,528,311 A | 7/1985 | Beard et al. |
| 4,575,373 A | 3/1986 | Johnson |
| 4,585,457 A | 4/1986 | Kalb |
| 4,604,295 A | 8/1986 | Humphreys |
| 4,615,701 A | 10/1986 | Woods |
| 4,620,954 A | 11/1986 | Singer et al. |
| 4,685,921 A | 8/1987 | Peyman |
| 4,685,922 A | 8/1987 | Peyman |
| 4,693,717 A | 9/1987 | Michelson |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,764,423 A | 8/1988 | Yamaguchi et al. |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turely |
| 4,902,293 A | 2/1990 | Feaster |
| 4,913,536 A | 4/1990 | Barnea |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,145,884 A | 9/1992 | Yamamoto et al. |
| 5,145,935 A | 9/1992 | Hayashi |
| 5,152,789 A | 10/1992 | Willis |
| 5,171,266 A | 12/1992 | Wiley et al. |
| 5,200,430 A | 4/1993 | Federman |
| 5,201,763 A | 4/1993 | Brady et al. |
| 5,203,788 A | 4/1993 | Wiley |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'Donnell, Jr. |
| 5,290,892 A | 3/1994 | Namdaran et al. |
| 5,326,347 A | 7/1994 | Cumming |
| 5,391,590 A | 2/1995 | Gerace et al. |
| 5,405,386 A | 4/1995 | Rheinish et al. |
| 5,443,506 A | 8/1995 | Garabet |
| 5,444,106 A | 8/1995 | Zhou et al. |
| 5,444,135 A | 8/1995 | Cheradame et al. |
| 5,476,514 A | 12/1995 | Cumming |
| 5,489,302 A | 2/1996 | Skottun |
| 5,496,366 A | 3/1996 | Cumming |
| 5,506,300 A | 4/1996 | Ward et al. |
| 5,512,609 A | 4/1996 | Yang |
| 5,578,081 A | 11/1996 | McDonald |
| 5,585,049 A | 12/1996 | Grisoni et al. |
| 5,593,436 A | 1/1997 | Langerman |
| 5,607,472 A | 3/1997 | Thompson |
| 5,628,795 A | 5/1997 | Langerman |
| 5,633,504 A | 5/1997 | Collins et al. |
| 5,665,822 A | 9/1997 | Bitler et al. |
| 5,674,282 A | 10/1997 | Cumming |
| 5,676,669 A | 10/1997 | Colvard |
| 5,697,973 A | 12/1997 | Peyman et al. |
| 5,702,441 A | 12/1997 | Zhou |
| 5,774,273 A | 6/1998 | Bornhorst |
| 5,776,191 A | 7/1998 | Mazzocco |
| 5,776,192 A | 7/1998 | McDonald |
| 5,843,188 A | 12/1998 | McDonald |
| 5,891,931 A | 4/1999 | Leboeuf et al. |
| 5,928,282 A | 7/1999 | Nigam |
| 5,964,802 A | 10/1999 | Anello et al. |
| 5,984,962 A | 11/1999 | Anello et al. |
| 6,013,101 A | 1/2000 | Israel |
| 6,015,842 A | 1/2000 | Leboeuf et al. |
| 6,102,539 A | 8/2000 | Tucker |
| 6,117,171 A | 9/2000 | Skottun |
| 6,124,980 A | 9/2000 | Cerbell |
| 6,139,576 A | 10/2000 | Doyle et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,348,437 B1 | 2/2002 | Avery et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,436,092 B1 | 8/2002 | Peyman |
| 6,443,985 B1 | 9/2002 | Woods |
| 6,450,642 B1 | 9/2002 | Jethmalani et al. |
| 6,464,725 B2 | 10/2002 | Skottun |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk, III et al. |
| 6,601,956 B1 | 8/2003 | Jean et al. |
| 6,610,350 B2 | 8/2003 | Suzuki et al. |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |

(56) References Cited

U.S. PATENT DOCUMENTS

| | | |
|---|---|---|
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,060,094 B2 | 6/2006 | Shahinpoor et al. |
| 7,068,439 B2 | 6/2006 | Esch |
| 7,122,053 B2 | 10/2006 | Esch |
| 7,217,288 B2 | 5/2007 | Esch et al. |
| 7,247,168 B2 | 7/2007 | Esch et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,438,723 B2 | 10/2008 | Esch |
| 7,485,144 B2 | 2/2009 | Esch |
| 7,494,505 B2 | 2/2009 | Kappelhof et al. |
| 7,763,069 B2 | 7/2010 | Brady et al. |
| 7,776,088 B2 | 8/2010 | Shadduck |
| 7,988,292 B2 | 8/2011 | Neal et al. |
| 8,162,927 B2 | 4/2012 | Peyman |
| 2001/0001836 A1 | 5/2001 | Cumming |
| 2001/0016771 A1 | 8/2001 | Cumming |
| 2001/0039449 A1 | 11/2001 | Johnson et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0088050 A1 | 5/2004 | Norrby et al. |
| 2004/0127984 A1 | 7/2004 | Paul et al. |
| 2004/0181279 A1 | 9/2004 | Nun |
| 2005/0021139 A1 | 1/2005 | Shadduck |
| 2005/0113911 A1 | 5/2005 | Peyman |
| 2005/0125000 A1 | 6/2005 | Tourrette et al. |
| 2005/0165410 A1 | 7/2005 | Zadno-Azizi et al. |
| 2005/0264756 A1 | 12/2005 | Esch |
| 2006/0069433 A1 | 3/2006 | Nun |
| 2006/0158611 A1 | 7/2006 | Piers et al. |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0203578 A1 | 8/2007 | Scholl et al. |
| 2007/0213817 A1 | 9/2007 | Esch et al. |
| 2007/0299487 A1 | 12/2007 | Shadduck |
| 2008/0015689 A1 | 1/2008 | Esch et al. |
| 2008/0046074 A1 | 2/2008 | Smith et al. |
| 2008/0046075 A1 | 2/2008 | Esch et al. |
| 2008/0200982 A1 | 8/2008 | Your |
| 2008/0306587 A1 | 12/2008 | Your |
| 2008/0306588 A1 | 12/2008 | Smiley et al. |
| 2009/0005865 A1 | 1/2009 | Smiley et al. |
| 2009/0027661 A1 | 1/2009 | Choi et al. |
| 2009/0030425 A1 | 1/2009 | Smiley et al. |
| 2009/0149952 A1 | 6/2009 | Shadduck |
| 2010/0131058 A1 | 5/2010 | Shadduck |
| 2010/0179653 A1 | 7/2010 | Argento et al. |
| 2010/0228344 A1 | 9/2010 | Shadduck |
| 2010/0228346 A1 | 9/2010 | Esch |
| 2011/0208301 A1 | 8/2011 | Anvar et al. |
| 2012/0078361 A1 | 3/2012 | Shadduck |
| 2012/0226351 A1 | 9/2012 | Peyman |
| 2013/0060331 A1 | 3/2013 | Shadduck |
| 2013/0250239 A1 | 9/2013 | Hildebrand et al. |
| 2013/0268070 A1 | 10/2013 | Esch et al. |
| 2014/0249625 A1 | 9/2014 | Shadduck |

FOREIGN PATENT DOCUMENTS

| | | | |
|---|---|---|---|
| JP | 07-044938 | 5/1995 | |
| JP | 8501715 | 2/1996 | |
| JP | 8224295 | 9/1996 | |
| JP | 9294754 | 11/1997 | |
| JP | 10-206609 | 8/1998 | |
| JP | 10-206609 A * | 8/1998 | ............... A61F 2/16 |
| JP | 11-47168 A | 2/1999 | |
| JP | 11056998 | 3/1999 | |
| JP | 11276509 | 10/1999 | |
| JP | 2001-502592 A | 2/2001 | |
| JP | 2003144387 | 5/2003 | |
| JP | 2003-524503 A | 8/2003 | |
| JP | 2003530978 | 10/2003 | |
| SU | 1810052 | 4/1993 | |
| WO | WO 97/06751 A | 2/1997 | |
| WO | WO 00/41650 A1 | 7/2000 | |
| WO | WO 00/64655 A1 | 11/2000 | |
| WO | WO 01/60286 A1 | 8/2001 | |
| WO | WO 01/89435 A1 | 11/2001 | |
| WO | WO 01/97742 A2 | 12/2001 | |
| WO | WO 02/051338 | 2/2004 | |
| WO | WO 2004/010895 A2 | 2/2004 | |

OTHER PUBLICATIONS

Gorder, P. F.; Electricity can pump medicine in implanted medical devices; Ohio State Research News; 3 pgs.; May 2, 2002 (printed from internet Aug. 19, 2010).

Lakes et al., "Dramatically stiffer elastic composite materials due to negative stiffness phase?," Journal of the Mechanics and Physics of Solids, vol. 50, pp. 979-1009, 2002.

Lakes, "A broader view of membranes," Nature, vol. 414, pp. 503-504, Nov. 29, 2001.

Lendlein et al., "Biodegradable, elastic shape-memory polymers for potential biomedical applications", Science; vol. 296; pp. 1673-1676; May 31, 2002.

(56) References Cited

OTHER PUBLICATIONS

Lendlein et al., "Shape-memory polymers," Angew. Chem. Int. Ed.; vol. 41; pp. 2034-2057; 2002.

Liu et al., "Thermomechanical characterization of a tailored series of shape memory polymers," Journal of Applied Medical Polymers, vol. 6, No. 2, 2002, pp. 47-52.

Baughman et al., "Negative poisson's ratios for extreme states fo matter," Science, vol. 288, pp. 2018-2022, Jun. 16, 2000.

Dubbelman et al.; The Thickness of the Aging Human Lens Obtained from Corrected Scheimpflug Images; Optometry & Vison Science; vo. 78; iss. 6; pp. 411-416; Jun. 2001.

Gordon, "Applications of shape memory polyurethanes," Proceedings of the First Intl Conf. on Shape Memory and Superelastic Tech., Asilomar Conference Center, Pacific Grove, CA, USA, pp. 115-120, 1994.

Gruber et al.; Exhaustive soxhlet extraction for the complete removal of residual compounds . . . ; Journal of Biomedical Materials Research; vol. 53; No. 5; pp. 445-448; Mar. 2000.

Jeon et al., "Shape memory and nanostructure in poly(norbornyl-POSS) copolymers," Polymer International, vol. 49, pp. 453-457, 2000.

Kim et al., "Polyurethanes having shape memory effects," Polymer, vol. 37, No. 26, pp. 5781-5793, 1996.

Lakes et al., "Extreme damping in composite materials with negative-stiffness inclusions," Nature, vol. 410, pp. 565-567, Mar. 29, 2001.

Lakes et al., "Microbuckling instability in elastomeric cellular sollids," J. Materials Science, vol. 28, pp. 4667-4672, 1993.

Lakes, "Extreme damping in compliant composites with a negative-stiffness phase," Philosophical Magazine Letters, vol. 81, No. 2, pp. 95-100, 2001.

Lakes, "Extreme damping in composite materials with a negative stiffness phase," Physical Review Letters, vol. 86, No. 13, pp. 2897-2900, Mar. 26, 2001.

Lakes, "Lateral deformations in extreme matter," Science, vol. 288, pp. 1976, Jun. 2000; 3 pgs.

Lakes, "Negative poisson's ratio materials," Science, vol. 238, pp. 551, Oct. 23, 1987.

Lakes, "No contractile obligations," Nature, vol. 358, pp. 713-714, 1992.

Li et al., "Crystallinity and morphology of segmented polyurethanes with different soft-segment length," Journal of Applied Polymer Science, vol. 62, pp. 631-638, 1996.

Mather et al., "Strain recovery in POSS hybrid thermoplastics," Polymer Preprints, vol. 41, No. 1, pp. 528-529, 2000.

Takahashi et al., "Structure and properties of shape-memory polyurethane block copolymers," Journal of Applied Polymer Science, vol. 60, pp. 1061-1069, 1996.

Tobushi et al., "Thermomechanical properties of shape memory polymers of polyurethane series and their applications," Journal de Physique IV, Colloque C1, vol. 6, pp. 377-384, 1996.

Vass et al.; Prediction of pseudophakic capsular bag diameter based on biometric variables; J Cataract Refract Surg.; vol. 25; pp. 1376-1381; 1999.

Wyant et al; "Basic Wavefront Aberration Theory for Optical Metrology," Applied Optics and Optical Engineering, vol. XI, 1992: pp. 1, 28-39.

Xu et al., "Basic negative poisson's ratio microstructures by soft lithography," Advanced Materials, vol. 11, No. 14, 1999, pp. 1186-1189, 1999.

Esch et al.; U.S. Appl. No. 12/853,892 entitled "Accommodating Intraocular Lens Having Peripherally Actuated Deflectable Surface and Method," filed Aug. 10, 2010.

Hildebrand et al.; U.S. Appl. No. 12/872,314 entitled "Lens Capsule Size Estimation," filed Aug. 31, 2010.

Scholl et al.; U.S. Appl. No. 13/193,487 entitled "Accommodating Intraocular Lenses," filed Jul. 28, 2011.

Smiley et al.; U.S. Appl. No. 13/193,983 entitled "Accommodating Intraocular Lenses," filed Jul. 29, 2011.

Smiley et al.; U.S. Appl. No. 13/194,004 entitled "Accommodating Intraocular Lenses," filed Jul. 29, 2011.

Hildebrand et al.; U.S. Appl. No. 13/180,427 entitled "Intraocular lens delivery devices and methods of use," filed Jul. 11, 2011.

Matthews, Gregory V.; U.S. Appl. No. 13/427,617 entitled "Intraocular Lens Loading Systems and Methods of Use," filed Mar. 22, 2012.

Smiley et al.; U.S. Appl. No. 13/672,608 entitled "Accommodating Intraocular Lenses and Methods of Use," filed Nov. 8, 2012.

Smiley et al.; U.S. Appl. No. 13/711,552 entitled "Accommodating Intraocular Lenses and Methods of Use," filled Dec. 11, 2012.

Lakes; Deformations in extreme matter; Science; perspectives; vol. 288; No. 5473; pp. 1976-1977; Jun. 16, 2000.

Matthews et al.; U.S. Appl. No. 13/835,876 entitled "Intraocular Lens Delivery Systems and Methods of Use," filed Mar. 15, 2013.

Hildebrand et al.; U.S. Appl. No. 14/163,794 entitled "Intraocular Lens Delivery Devices and Methods of Use," filed Jan. 24, 2014.

* cited by examiner

INTRAOCULAR LENS SYSTEM AND METHOD FOR POWER ADJUSTMENT

CROSS-REFERENCE TO RELATED APPLICATIONS

This application is a continuation of U.S. application Ser. No. 11/069,136, filed Feb. 28, 2005, now U.S. Pat. No. 7,776,088, which application is a continuation of U.S. application Ser. No. 10/231,433, filed Aug. 29, 2002, now abandoned, which claims benefit of U.S. Provisional Appln. No. 60/316,203, filed Aug. 31, 2001, all of which are incorporated herein by reference.

BACKGROUND OF THE INVENTION

1. Field of the Invention

The present invention is directed to intraocular lenses (IOLs) that define an optical power that is adjustable following implantation. More particularly, the IOL is adapted for use in cataract patients that require an adjustment in the optical power of the lens post-implantation.

2. Description of the Related Art

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens implantation is the preferred method of treating the functional limitations. In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age-related cataract conditions are the most common.

In treating a cataract, the surgeon removes material from the lens capsule and replaces it with an intraocular lens (IOL) implant. The typical IOL provides a selected focal length that allows the patient to have fairly good distance vision. Since the lens can no longer accommodate, the patient typically need glasses for reading.

The surgeon selects the power of the IOL based on analysis of refractive characteristics of the patient's eye prior to the surgery. In a significant number or cases, after the patient's eye has healed from the cataract surgery, there is a refractive error that could not be predicted. There remain substantial difficulties in calculating the proper power of an IOL for any particular patient. To solve any unpredicted refractive errors following IOL implantation, the ophthalmologist can perform a repeat surgery to replace the IOL—or the patient can live with the refractive error that may require prescription eyeglasses for both near and distant vision. What is needed is an IOL that carries means for adjusting its power post-implantation, as well as for treating astigmatisms.

BRIEF SUMMARY OF THE INVENTION

The present invention provides an intraocular lens (IOL) that comprises first and second surface portions that are assembled to provide an interior space or chamber within the interior of the lens for allowing fluid flows therein to alter at least one surface portion of the lens to thereby alter optical parameters of the IOL. In an exemplary embodiment, the first and second surface portions extend to the lens body periphery wherein a first portion of the interior chamber extends within the central optic lens element. A peripheral portion of the interior chamber extends about the lens periphery. The invention further provides a microporous or nanoporous body that is intermediate the central and peripheral regions of the interior chamber portions. In one embodiment, the microporous or nanoporous body is capable of cooperating with an external Rf or light source to expose a charge to a charge-carrying fluid within the interior chamber. By this means, fluid flows are induced to alter the optical parameters of the lens.

In another preferred embodiment, the coincident surfaces of the first and second lens portions that bound the interior chamber are configured with projecting shape structures that cooperate with one another and fluid movement to (i) amplify the dynamic range of surface curvature modification and further (ii) to insure that the first and second lens portions are mechanically coupled to allow controlled shape change.

In another preferred embodiment, the lens body is fabricated of first and second structural portions of first and second polymer types. The first structural portion and first polymer type can comprise the substantial part of the optic element, and is a stable, flexible polymer as is known in the art. The second polymer is dimensionally-sensitive to light energy and is thus formed into a second structure that can be controllably changed in shape to move fluids within the interior of the lens or to otherwise directly, or indirectly, deform the first structural portion to alter the optical parameters of the IOL.

BRIEF DESCRIPTION OF THE SEVERAL VIEWS OF THE DRAWINGS

In order to better understand the invention and to see how it may be carried out in practice, some preferred embodiments are next described, by way of non-limiting examples only, with reference to the accompanying drawings, in which.

DETAILED DESCRIPTION OF THE INVENTION

Figure 1:
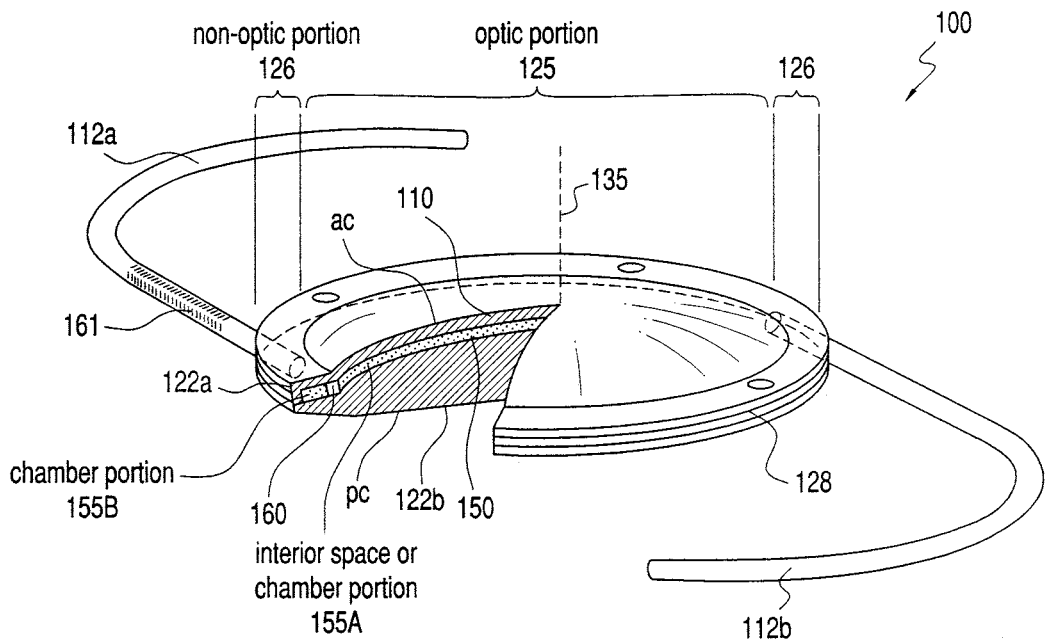
FIG. 1 is a perspective view of a Type "A" intraocular lens in accordance with one embodiment of the invention.
Figure 2:
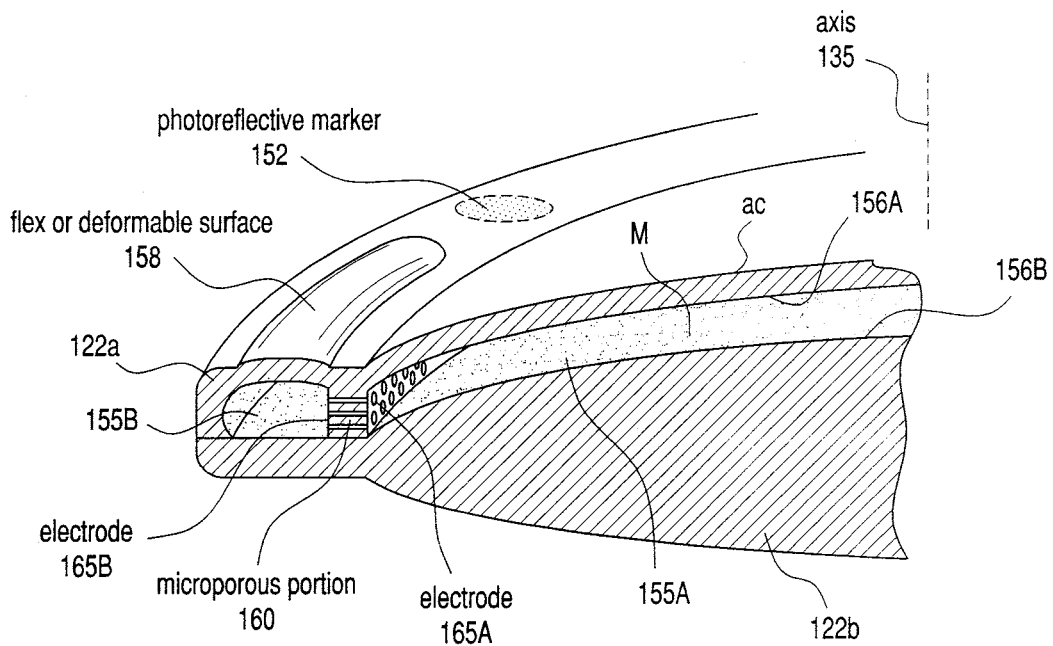
FIG. 2 is a sectional view of a portion of the intraocular lens shown in FIG. 1 in a first shape.

1. Type "A" intraocular lens. FIGS. 1 and 2 illustrate an intraocular lens 100 (IOL) in accordance with the invention in which the lens body has at least one flexible or deformable surface element 110 that allows for a change in its shape or curvature to adjust the optical parameters of the lens. Deformation and shape adjustment of the surface element 110 in preferred embodiments is caused by fluid flows with an interior space of the lens to displace the surface element, when coupled with energy or stimulus from an external source 115 (see FIG. 4). In an exemplary embodiment, the IOL body 100 is coupled to a haptic portion that comprises radially-extending struts (or haptics) indicated at 112a and 112b in FIG. 1 that are coupled to the lens perimeter. Typically, the haptics 112a and 112b have radial-outward ends that define arcuate terminal portions. The haptics 112a and 112b have a particular length so that the terminal portions create a slight engagement pressure when in contact with the equatorial region of the capsular sac after being implanted. The diameter of outermost portions of the haptics is typically about 13.0 mm., and the diameter of the lens body 110 is about 4.5 mm. to 7.5 mm.

In the embodiment illustrated in FIGS. 1 and 2, it can be seen that lens 100 comprises an assembly of an anterior lens portion 122a with its deformable surface element 110 defining an anterior curvature ac. The lens further has a posterior lens portion 122b with its exterior surface defining a posterior curvature pc. The lens portions 122a and 122b define a central optic portion 125 with axis 135 that comprises transparent optic element of the IOL for focusing light on the retina. In one embodiment, the lens defines a peripheral non-optic portion 126 that is outward of the optic element, and the lens portions 122a and 122b typically are bonded together at or about bond line 128 in this peripheral non-optic portion 126. The lens 100 thereby defines and interior space or chamber 150 that further defines a first interior space or chamber portion 155A within the central optic portion 125.

The lens portions 122a and 122b are fabricated of a transparent, flexible material, such as a silicone polymeric material, acrylic polymeric material, hydrogel polymeric material or the like, all of which known in the art of IOL fabrication and allow the lens to be rolled or folded for introduction into the eye through a small incision. As will be described below, the functionality of the lens depends on flexibility or deformability of at least one lens surface, which in the exemplary embodiment of FIGS. 1 and 2 is the central wall portion 110 of the anterior element 122a. The lens body, or at least one surface portion thereof, also can be fabricated of a slightly stiffer biocompatible material if very thin in cross section, such as polymethyl methacrylate (PMMA). Thus, it is possible that the anterior and posterior surfaces 122a and 122b that can be formed of different materials such as silicone and PMMA. The lens optic, depending on the material, can be injection-molded, fabricated with casting techniques or turned by a lathe as is known in the art.

As can be seen in FIGS. 1 and 2, the lens carries a plurality of reflective markings 152 in any location outward of the periphery of the optic portion 125. These markings 152 are adapted in some embodiments to cooperate with a light source, photo-sensing system, scanner and eye-tracking system as is known in the art to direct and localize a light beam at a selected location or locations of the lens 100 for energy delivery thereto.

In the embodiment of FIGS. 1 and 2, the central optic portion 125 is depicted as bi-convex in sectional view, with its anterior and posterior surface curvatures ac and pc having a similar convex shape. It should be appreciated that the posterior lens element may have any selected curvature and the combination of the anterior and posterior lens surfaced can define a lens shape that is plano-convex, convexo-concave, or plano-concave. Also, either or both anterior and posterior lens elements can have multiple concentric powers as in known in the art of multi-focal lens design.

The haptics or strut members can be polypropylene or like polymeric materials, coupled to the periphery portion 126 and thus extend outwardly to engage the perimeter wall of the capsular sac to maintain the lens in a desired position. The haptics can be glued or welded to the periphery portion 126 or molded along with a portion of the lens. While the configuration of the haptics of the lens shown in FIG. 1 is typical, it should be appreciated that any plate haptics or other types of haptic also are possible.

Figure 3:
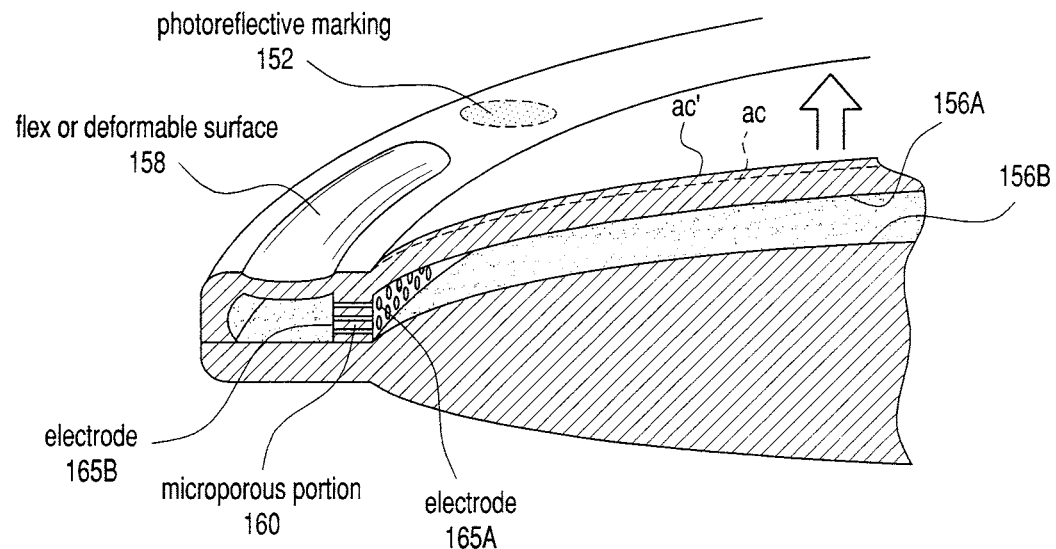
FIG. 3 is a sectional view of the lens portion of FIG. 2 in a second shape.

As can be seen in FIGS. 2 and 3, the lens body 100 defines an interior space or chamber 150 that is sealed from the exterior environment and that carries a selected fluid media M. The chamber 150 further defines a first chamber portion or central space 155A wherein a change in fluid volume therein will flex and displace lens wall portion 110. The lens further defines a second (peripheral) chamber portion or space 155B in the peripheral portion 126 of the lens. In FIGS. 2 and 3, for clarity of explanation, the central space 155A is illustrated as having a substantial axial sectional dimension thereacross, but it should be appreciated that the coincident surfaces 156A and 156B of the lens on opposing sides of the space 155A may rest in substantial contact with one another in one position and only be slightly spaced apart from one another in a power-adjusted position.

Of particular interest, a microporous body portion indicated at 160 lies intermediate the first and second chamber portions 155A and 155B. As will be described below, the invention describes means for causing fluid flow from the peripheral chamber portion to the central chamber portion, or vice versa, to alter the shape and optical parameters of the optic portion 125. The terms fluid flow, migration, perfusion and diffusion through the microporous body portion 160 are used interchangeably herein to describe any fluid movement through the microporous portion 160, which also may be described for convenience as porous, microporous, fluid-permeable, fluid-diffusible or fluid-migratable. The microporous body portion 160 can consist of a small section of the body between the first and second chambers, for example, it can extend from 1° to 5° in a radial angle about the lens. Alternatively, the microporous body portion 160 can extend in 360° around the lens between the first and second chamber portions 155A and 155B. As will be described in more detail below, a lens corresponding to the invention may have a plurality of cooperating central and peripheral chambers, in which case each pair of cooperating chambers would be have an intermediate microporous body portion 160. The use of the term "microporous" to describe the fluid-permeable material 160 between the first and second chambers 155A and 155B, and encompasses "nanoporous" materials that allow fluid migration therethrough. More specifically, the cross-sectional dimension of the flow passageways 161 in material 160 for use in the invention range from about 5 nanometers to about 25 microns. More preferably, the cross-sectional dimensions of the flow passageways 161 range from about 100 nanometers to about 5 microns. The microporous material 160 typically is a networked porous polymer wherein the maximum cross-section of a flow passageway therein corresponds to the dimensional ranges described above. The microporous material 160 can be a porous polymer such as a biocompatible polysiloxane, polyurethane, PFTE, polyacrylate, polyamide, polyester, polyolefin, nylon or co-polymers thereof. Many means are known in the art for creating microporous polymers and need not be described further herein. The microporous material 160 also encompasses ordered or nanostructured assembled materials that have pores or channels therein that correspond to the dimensional ranges above. In another preferred embodiment, the microporous material 160 can be a micromachined microchannel material 160 with any suitably shaped channels therein. Such a typically rigid material can be insert-molded into lens. In one such material embodiment, the microchannel structure can be fabricated in silicon by NanoSciences Corporation, Hurley Farms Industrial Park, Bldg. 3, 115 Hurley Rd., Oxford, Conn. 06478. A suitably dimensioned microchannel structure can be fabricated in silicon with high-aspect ratio channel in the range of somewhat less that 1 micron to about 8 microns by NanoSciences Corp. Further, the company's proprietary technology allows for deposition of conductive surfaces within, or at end surfaces of, the microchannels which is useful in some embodiments of the invention disclosed herein.

Referring to FIG. 3, means are provided for causing fluid migration through the microporous material 160, which in one embodiment utilizes energy from an external source to activate charge-carrying circuitry in the lens to provide a charge at an electrode surface 165A and/or 165B within or about ends of the channels that extend through the microporous body 160. To cooperate with such a charge, the fluid media M in the respective chambers portions 155A and 155B carries a charge so that it responds to an electrical energy field created at or about one or more electrodes to thereby cause fluid flow. In FIG. 3, it can be understood that electrode surfaces 165A and 165B are on opposing sides of the microporous body 160 and thus can carry fluid between the first and second chambers 155A and 155B. For example, a charge applied to an electrode surface can cause the charged fluid media M to migrate from the peripheral chamber portion 155B to the central chamber portion 155A (see FIG. 3) thereby altering the anterior curvature of the central optic portion from ac to ac'. The fluid media M can be any flowable media with a charge attached, and in one embodiment can be a saline solution. In another embodiment, the fluid media M can be matching index fluid such as a silicone polymer. The electrodes surfaces can be any type of conductive material, and in one embodiment is a thin film layer of gold, platinum, tantalum or the like. The use of an electrical charge to cause flows in a microchannel or nanochannel is known in the art, and for example is described in the following materials which are incorporated herein by this reference: Conlisk et al. Mass Transfer and Flow in Electrically Charged Micro- and Nanochannels, Analytical Chemistry, Vol. 74 Issue 9, pp. 2139-2150; article titled Electricity Can Pump Medicine in Implanted Medical Devices, http://www.sciencedaily.com/releases/2002/05/02050607454-7.htm. Thus, FIG. 3 shows the lens 100 wherein fluid flow from the periphery into the central space 155A cause a change in the lens curvature from ac to ac'.

FIGS. 2 and 3 illustrate another feature of the lens wherein a deformable wall portion 158 of the lens adjoins the peripheral chamber portion 155B to allow an addition to or depletion of the fluid media M in that chamber portion. In other words, the deformable wall portion 158 is substantially thin and will "oil-can" to insure that charge-induced flow of media M will occur without restriction. FIG. 2 illustrates the wall portion 158 in a first condition, and FIG. 3 shows the deformable wall 158 in a second condition that is consistent with fluid flow into the central chamber portion.

Figure 4:
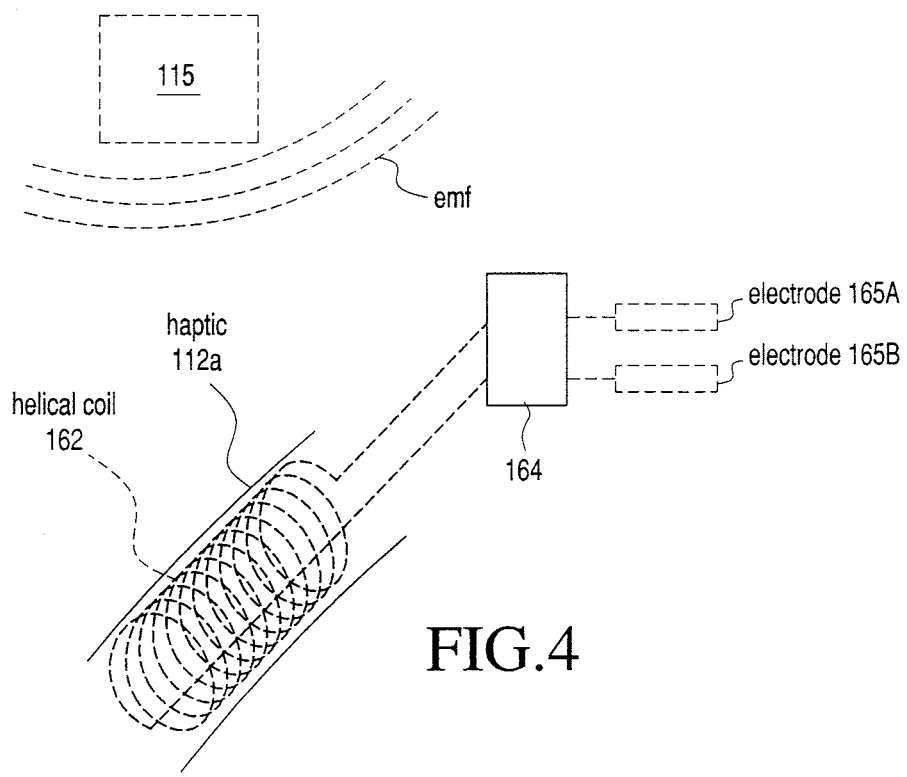
FIG. 4 is a schematic view of a component of the external energy application system of the lens of FIG. 1.
Figure 5:
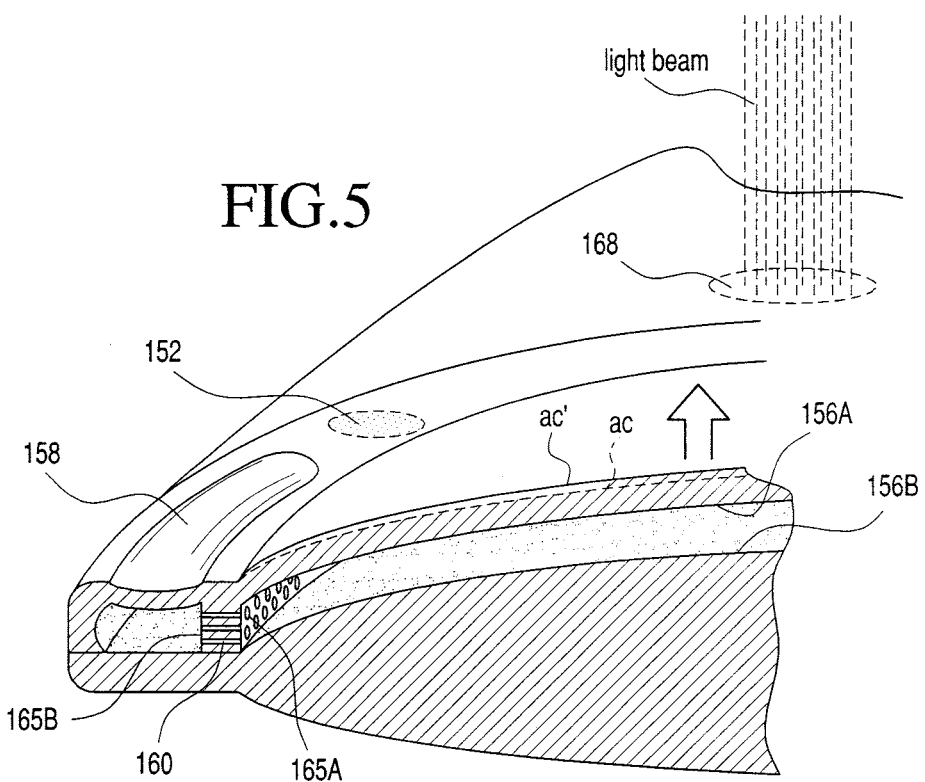
FIG. 5 is a schematic view of an alternative external energy application system that cooperates with a lens similar to that of FIGS. 1-3.

Now turning to FIG. 4, one embodiment of the system for applying energy to the lens from an external source comprises a helical coil 162 carried in a haptic element 112a and or 112b and tuned circuitry components 164 within the lens including electrical leads to the electrodes in the lens interior described above. The coil 162 is tuned with respect to a first selected frequency from a remote external radiofrequency source 115 (shown schematically in FIG. 4) as is known in the art. Thus, electromagnetic energy (indicated by waves or electromagnetic field emf in FIG. 5) can be received by the tuned circuitry to generate electrical potential and current flow in the implant circuitry. In one embodiment, the second haptic 112b carries another coil that is tuned to a second selected frequency, with the positive and negative electrodes reversed with respect to the first and second chambers to cause fluid media M to migrate from the central chamber 155A to the peripheral chamber 155B to reverse the curvature change in the optic portion. It should be appreciated that the coils 162 can be carried in any part of the lens of the invention-not just the haptics. The circuitry can also carry at least one capacitor for transient energy storage, to assist the physician in the operation of altering the power of the lens. FIG. 5 illustrates an alternative embodiment wherein a light source with a selected wavelength is targeted on the lens wherein a photoelectric cell or element 168 as is known in the art is adapted to create an electrical charge at the electrodes 165A and 165B to cause fluid migration as otherwise described above. In FIG. 5, the photoelectric cell 168 is indicated schematically as when carried in a plate haptic, and in this case the marking 152 can cooperate with a light beam and sensor to allow localization of a light beam upon the cell 168.

Figure 6A:
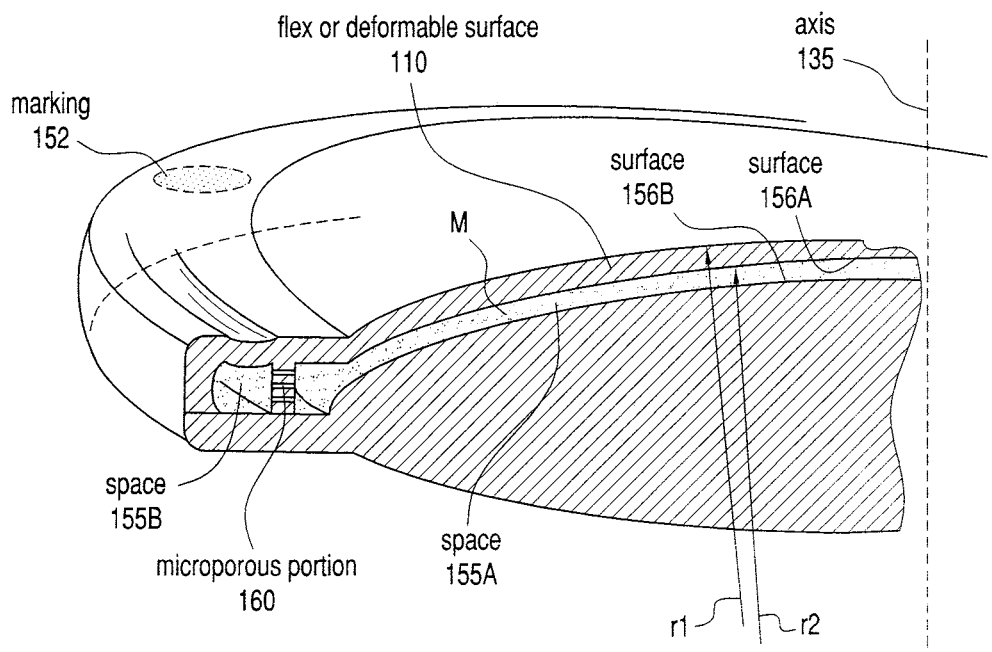
FIG. 6A is a sectional view of a portion of an IOL similar to that of FIGS. 1-3 wherein the deformable anterior element of the lens is uniform in cross-sectional dimension to provide a selected shape deformation upon an increase in fluid pressure at the lens interior.
Figure 6B:
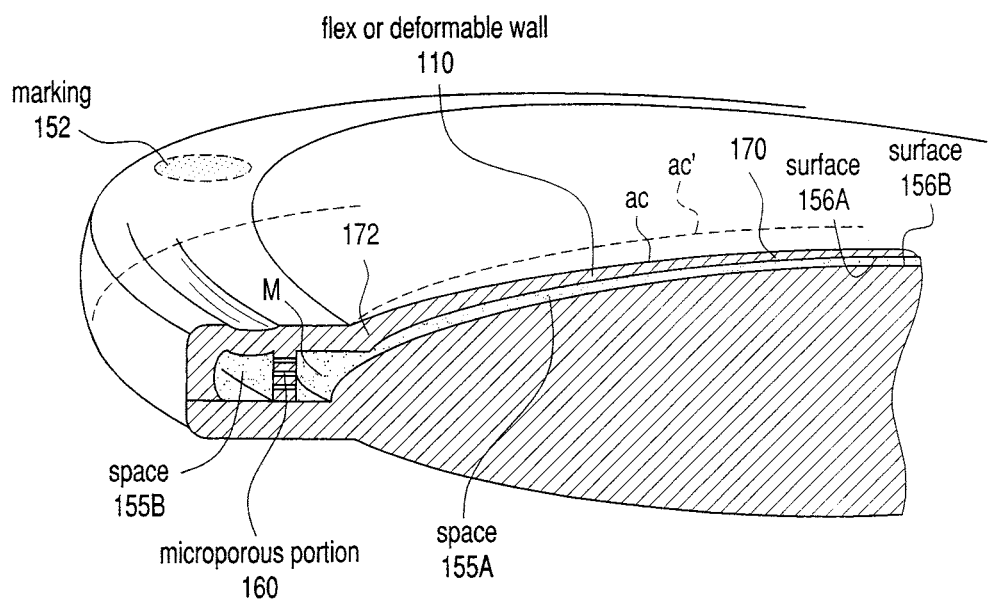
FIG. 6B is a sectional view similar to that of FIG. 6A with the deformable anterior element of the lens having a first non-uniform cross-sectional dimension to provide a different shape deformation upon an increase in fluid pressure at the lens interior.
Figure 6C:
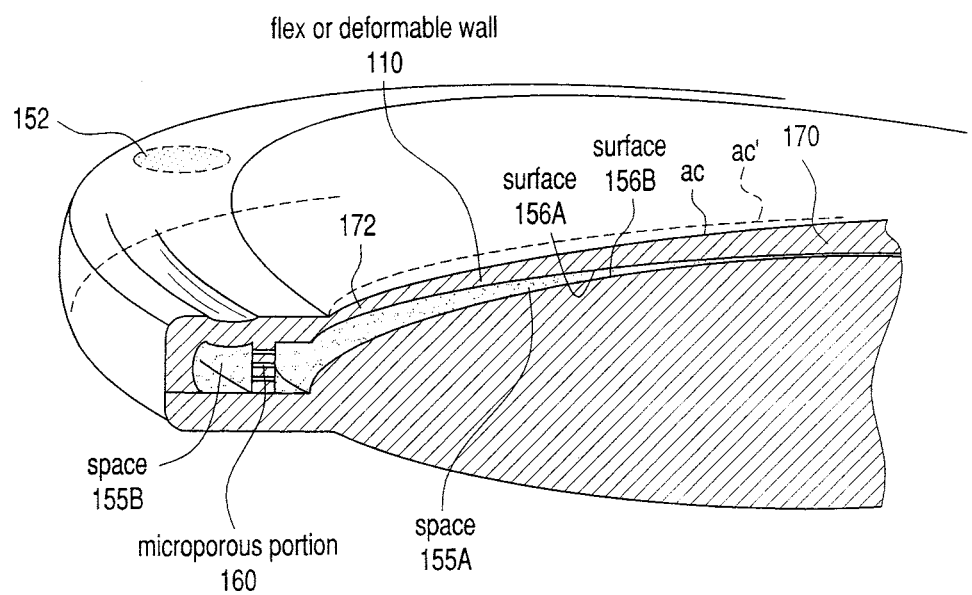
FIG. 6C is a sectional view similar to that of FIGS. 6A-6B with the deformable anterior element having a second non-uniform cross-sectional dimension to provide a different shape deformation upon an increase in fluid pressure at the lens interior.

FIGS. 6A-6C illustrate cross-sectional views of the flexible or deformable central lens wall 110 on the anterior side of the fluid-filled central chamber portion 155A wherein the deformable wall 110 can have a uniform thickness or more preferably a non-uniform thickness extending outward from the lens axis 135. Another way of describing the deformable wall 110 is that the anterior lens curvature ac and coincident surface 156A have non-concentric radii—and in some preferred embodiments the coincident surface 156A has a non-singular radius and consists of projecting portions thereby defining a plurality of radii.

By way of illustration, FIG. 6A illustrates the deformable or displaceable wall 110 with a uniform sectional thickness and concentric radii $r_1$ and $r_2$. FIG. 6B illustrates the displaceable wall 110 with a non-uniform sectional thickness wherein the lens wall transitions from a lesser cross-sectional dimension about axis 135 to a greater cross-sectional dimension radially outward from the optical axis. It can be understood that addition of fluid media M to the central chamber portion 155A will tend to displace, flex, deform or stretch the thinner central wall portion 170 to a greater extent than the radially outward region indicated at 172. This effect will tend to steepen the anterior lens curvature which is indicated at ac'.

FIG. 6C illustrates wall 110 again with a non-uniform sectional thickness wherein the wall transitions from a greater cross-sectional dimension about axis 135 to a lesser cross-sectional outwardly from the optical axis. In this case, addition of fluid media M to the central chamber portion 155A will tend to displace or deform the thinner outer wall portion 172 to a greater extent than the central region 170 which can be adapted to flatten the anterior lens curvature, is indicated at ac'.

Figure 7:
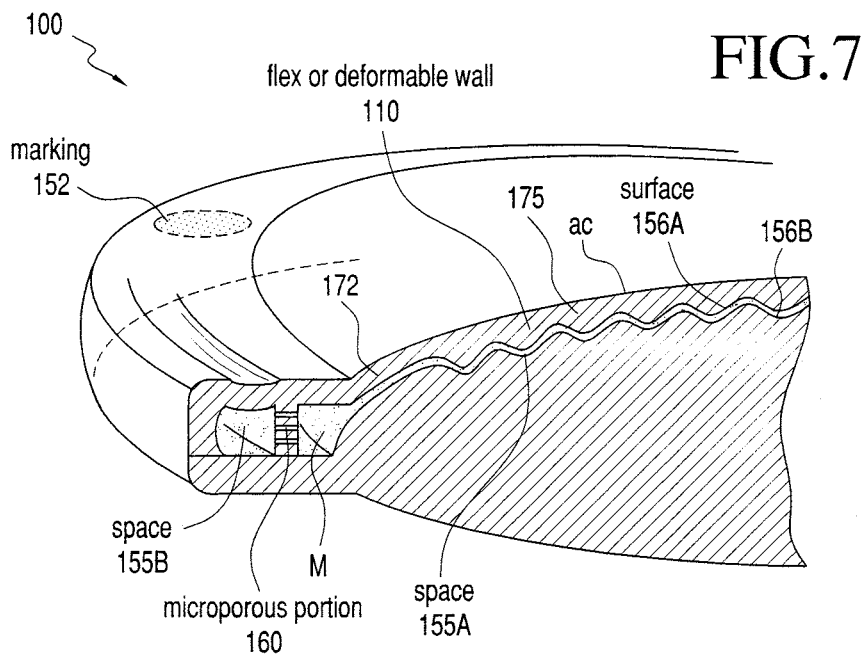
FIG. 7 is a perspective cut-away view of an alternative IOL with cooperating shape structures in coincident surfaces at an interior of the lens.
Figure 8A:
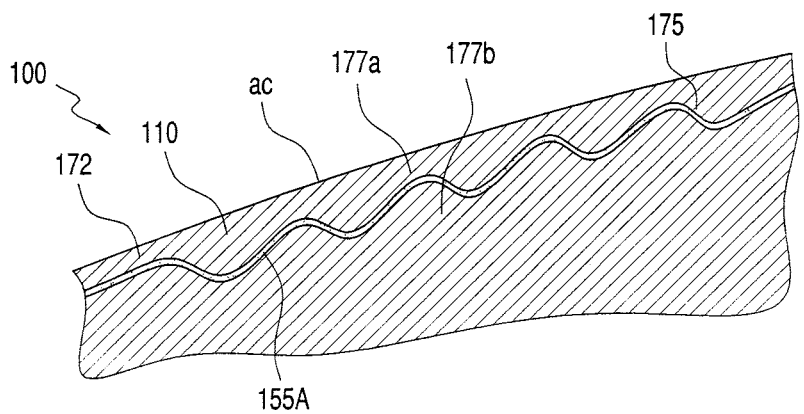
FIG. 8A is an enlarged sectional of the IOL of FIG. 7 taken along line 8-8 of FIG. 7 showing the shape structures and coincident surfaces in a first position.
Figure 8B:
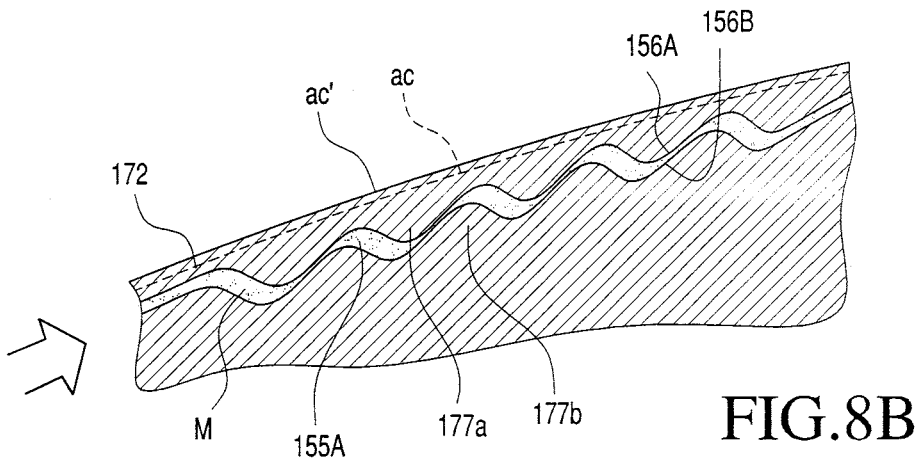
FIG. 8B is a sectional of the lens of FIG. 8A showing the cooperating shape structures and coincident surfaces in a second position.

FIG. 7 illustrates an alternative preferred embodiment of a lens 100 wherein the cross-sectional shape of the flexible or deformable anterior wall 110 adjacent the central chamber portion 155A carries interior surface relief structures 175 (collectively) for enhancing or controlling deformation of the wall 110. In one embodiment, referring to FIGS. 7 and 8A, the lens has coincident surfaces 156A and 156B on anterior and posterior sides of chamber portion 155A that define non-constant radii and more specifically a plurality of cooperating shape structures 177a and 177b that define a plurality of radii. These shape structures 177a and 177b are adapted to contact one another and move relative to one another very slightly to amplify or control the displacement of wall portion 110 when fluid media M migrates into the space or chamber portion 155A. Comparing FIGS. 8A and 8B, it can be seen that a very slight additional volume of fluid media M in space 155A will cause a predetermined stretch or deformation in thin outer region 172 to thereby cause shape structure 177a in anterior lens portion 110 to move relative to shape structure 177b in the posterior lens portion which thereby controllably alters anterior curvature from ac to ac'. It can be understood that the shaped structure of the coincident surfaces 156A and 156B can define a plurality of projecting portions in the form of annular elements, or alternatively a plurality of spaced apart surface relief elements. By comparing FIGS. 8A and 8B, the volumetric change in space 155A can be seen; in FIG. 8A the space is very thin and is a "potential" space and in FIG. 8B the volume of space 155A is increased. The further advantage of the lens design of FIGS. 8A and 8B is that in the adjusted shape of FIG. 8B, the shape structures on either side of space 155A are in contact to thereby provide a "mechanical" support between the lens surfaces rather than a fluid or hydraulic support as depicted in the embodiment of FIGS. 2, 3 and 6A for example. The more mechanical connection between the lens portions that carry anterior and posterior surfaces allows for adjustment to known precise dimensions and therefore optical parameters. In these embodiments, the lens system preferably uses an index-matching fluid.

Figure 9:
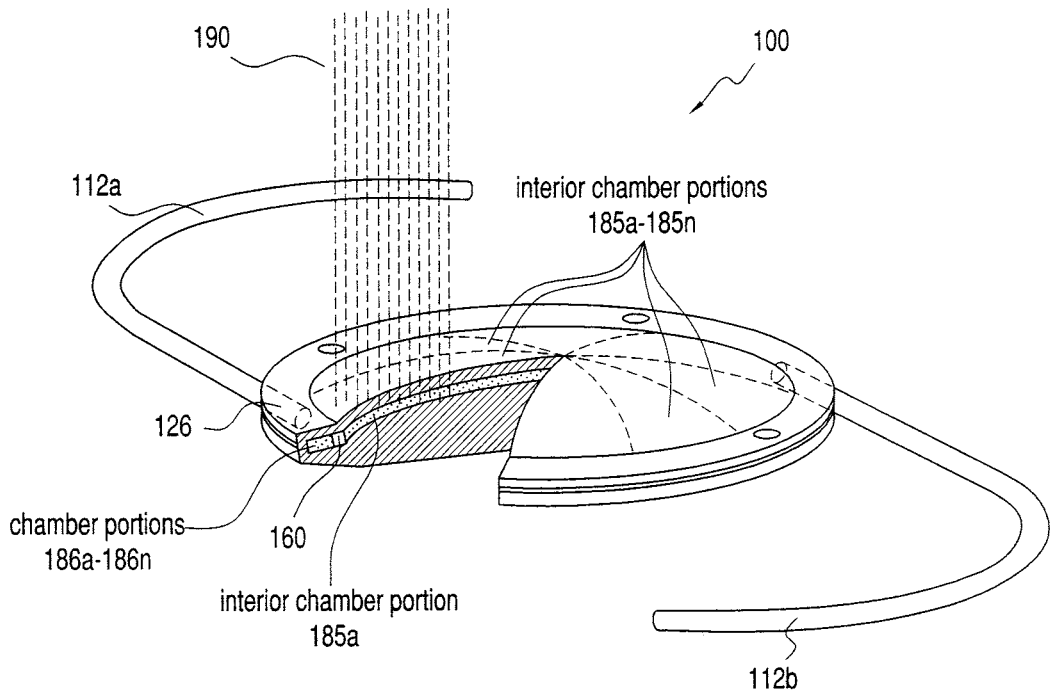
FIG. 9 is a perspective view of another embodiment of IOL with hydrogel microporous structure between first and second interior chamber portion together with a light beam illustrating its method of causing fluid flow in a first direction.
Figure 10:
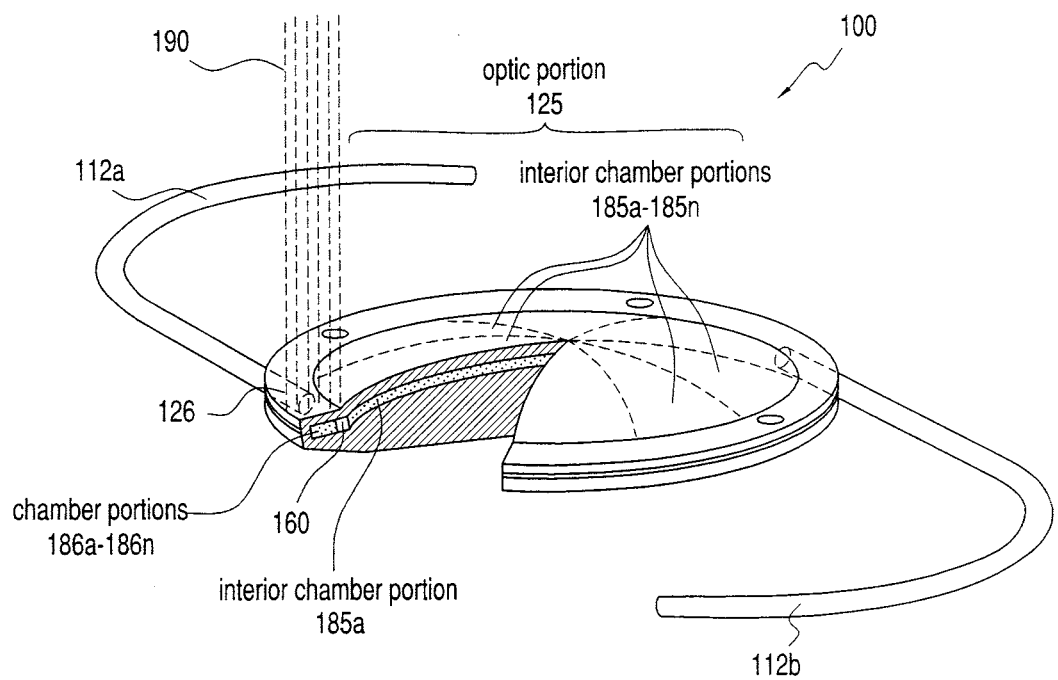
FIG. 10 is another perspective view of the IOL of FIG. 9 with a light beam causing fluid flow in a second direction.

FIGS. 9 and 10 illustrate an alternative embodiment of lens 100 wherein the lens carries a plurality of spaces or central chamber portions 185a-185n (where n is an integer) that each can receive or expel fluid flows therefrom to locally adjust lens shape. Such a lens would be useful for treating astigmatisms. Each chamber portion 185a-185n communicates through a microporous structure 160 (collectively) with a peripheral chamber portion 186a-186n so that the system operates as described previously. Preferably, the deformable anterior wall 110 and the coincident surfaces 156A and 156b carry interior surface relief structures 175 as described previously. The fluid flow means can be as described previously; however, FIGS. 9 and 10 illustrate another preferred system. In this embodiment, the microporous structure 160 is fabricated of a hydrogel material that is adapted to open and close its porosities based on a very slight change in temperature of the hydrogel. Thus, the hydrogel microporous structure 160 at 37° C. is designed to be closed to fluid flow therethrough. In FIG. 9, it can be seen that a light beam 190 is directed in part at the hydrogel microporous structure 160 which alters it from its non-porous state to its porous state. At the same time, the light beam is localized to overlap and impinge upon the targeted space, for example space 185a, which elevates the temperature of fluid media M therein and its expansion causes a portion of the fluid to migrate from the center to the peripheral chamber portion. In FIG. 10, the localization of the light beam 190 moves to overlap the hydrogel microporous structure 160 and the lens periphery, which will then move fluid media M inwardly. The light beam can be scanned to treat several chamber segments at once.

Figure 11:
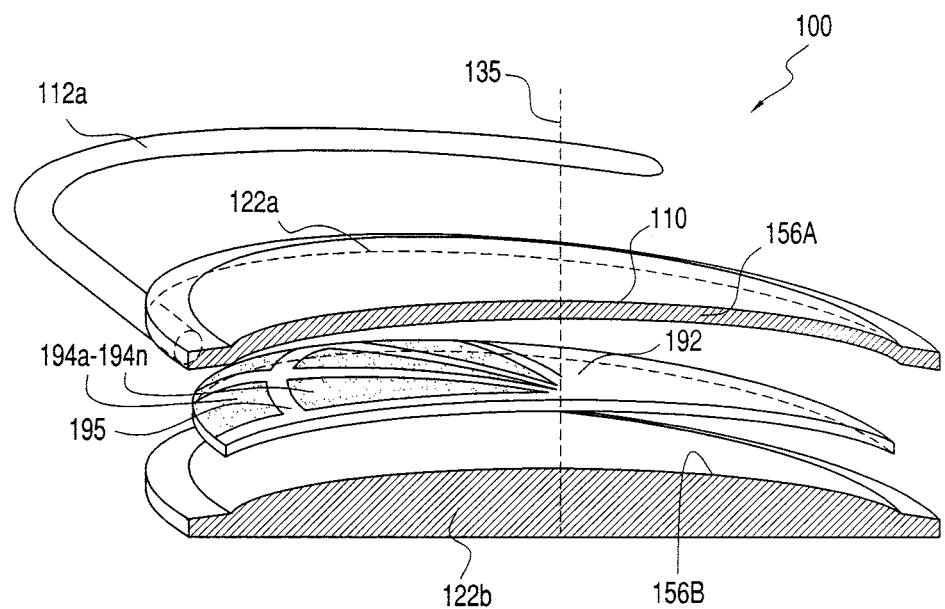
FIG. 11 is an exploded plan view of an IOL similar to that of FIGS. 9-10 showing a hydrogel layer of the lens.

FIG. 11 illustrates an exploded view of an alternative embodiment of lens 100 wherein the novel hydrogel microporous structure 160 is extended to the interior of the lens. The illustration of FIG. 11 further illustrates that the fabrication and assembly of a "switchable porosity" hydrogel lens is not complex. In FIG. 11, the anterior and posterior lens elements 122a and 122b are dimensioned to receive a layer 192 of a hydrogel material. Of particular interest, the layer 192 consists of a series of open or porous (non-switchable) hydrogel sections 194a-194n that are bounded by a selected pattern of switchable porosity hydrogel sections indicated at 195. As can be easily understood from the previous description, a localized light beam can alter a targeted site of a hydrogel boundary 195 to an open porosity and simultaneously heat and move a free fluid media M from within the porous (non-switchable) hydrogel sections 194 through the targeted location. Of particular interest, this system would allow for movement of fluid media M in any direction between hydrogel sections 194a-194n. It should be appreciated that any number of chamber portions, in any dimension and in any pattern whether radial, angular, concentric, or any combination thereof.

Figure 12A:
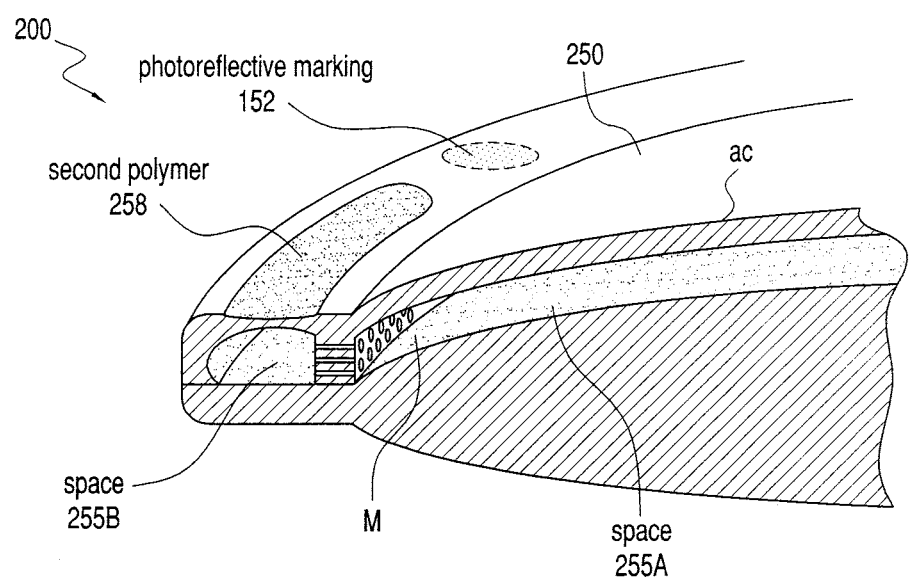
FIG. 12A is a sectional view of an alternative Type "B" intraocular lens wherein a light source is used to create thermal effects in a wall portion adjacent a fluid-filled chamber to cause fluid flows therefrom.
Figure 12B:
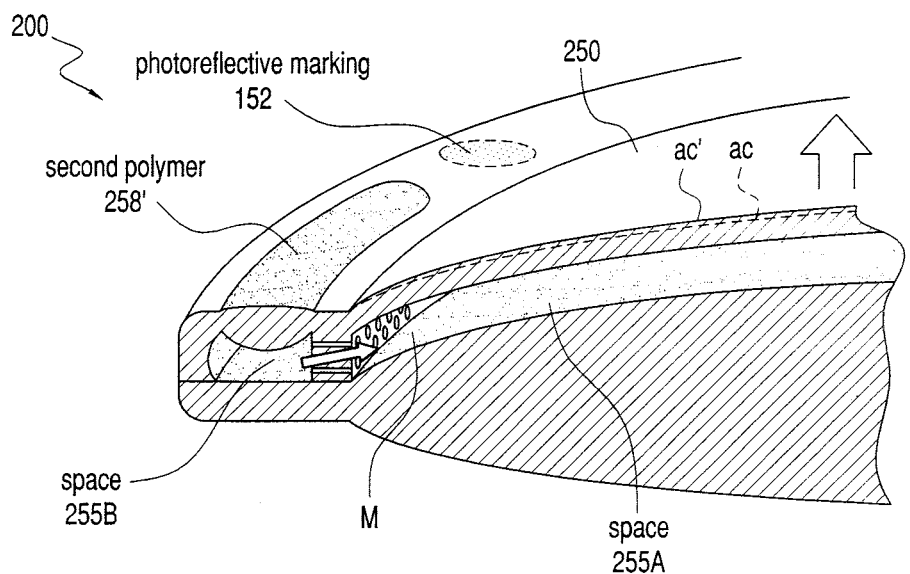
FIG. 12B is another view of the intraocular lens of FIG. 12A showing the thermal effects in the wall portion adjacent a fluid-filled chamber.

2. Type "B" intraocular lens. FIGS. 12A and 12B illustrate another alternative embodiment of intraocular lens 200 according to the invention which is similar to the Type "A" embodiment of FIGS. 1-3. In this embodiment, a light source is used in a different manner to induce fluid flows to a central chamber portion 255A from a peripheral chamber portion 255B, or vice versa. As illustrated in FIG. 12A, the lens comprises a first structure of a first polymer 250 and the lens carries at least one deformable wall portion 258 or second structure of a second polymer, which can be within a portion of the lens periphery, the entire lens periphery, or in the optic portion itself. The second polymer comprises a polymer that will change in dimension in response to light irradiation targeted on the second structure. In this case, the deformable wall portion 258 or second structure is adapted to swell upon irradiation, which is caused by thermal or chemical effects therein. As can be seen comparing FIGS. 12A and 12B, altering the deformable wall portion 258 from its first shape (FIG. 12A) to its second shape 258' (FIG. 12B) will reduce the volume of the peripheral chamber portion 255B thereby forcing fluid media M into the central chamber portion 255A to alter lens curvature as described above. Many polymers can be designed to expand upon irradiation, such as partially polymerized biocompatible urethanes, silicones, acrylics and co-polymers thereof. Polymers also can be designed to shrink as well known in the art of heat-shrink polymers. Preferably, such polymers are selected to be transparent to visible light. Thus, a lens is fabricated of a first stable polymer that is not dimensionally sensitive to light together with elements in portions of the lens that are dimensionally sensitive to light irradiation. The dimensionally-sensitive elements can be at a surface of the lens or within an interior portion of the lens. The dimensionally-sensitive element or elements can also comprise a floating element within a chamber of the lens, or a shape structure attached to a lens element that interfaces with a fluid-filled chamber. Also, the second material that dimensionally sensitive can be entirely embedded within the first polymer material that is stable but deformable, wherein expansion of the second material (dimensionally-sensitive) will deform and stress the first polymer material that is flexible. The scope of the invention thus includes the utilization of irradiation-sensitive polymers that undergo a shape change due to thermal or chemical interactions, and placing such polymers adjacent to a fluid volume in an interior of an intraocular lens wherein a polymer dimensional change cooperates with fluid migration with a resulting shape change in the lens. Several configurations of IOLs with (i) fluid permeable chamber portions and (ii) cooperating dimensional-change polymers are possible and fall within the scope of the invention and need not be described in further detail. The chamber portions can be in the central optic portion or a lens portion that is peripheral to the optic portion, or in both locations. The dimensional-change polymer likewise can located in the central optic portion or a lens portion that is peripheral to the optic portion, or in both locations.

Figure 13:
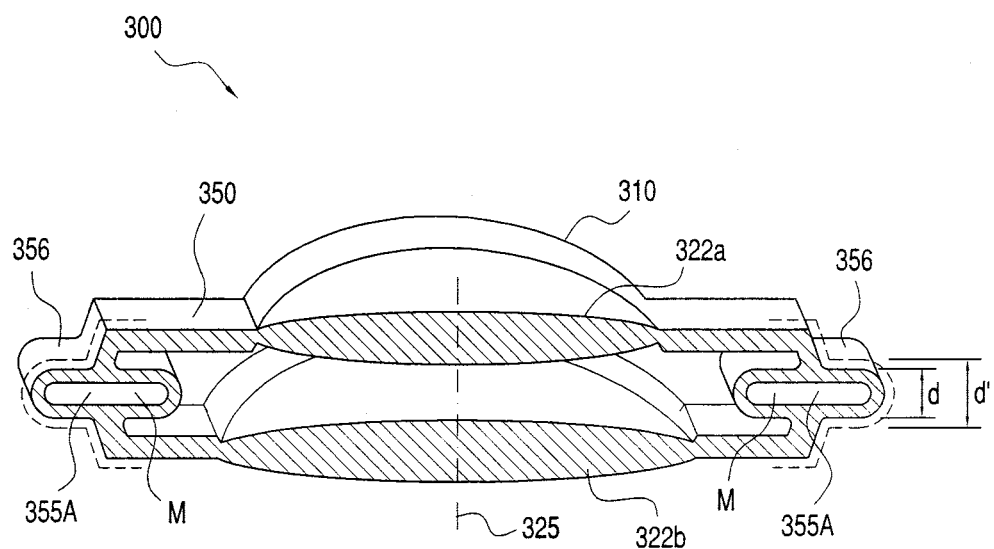
FIG. 13 is a sectional view of an alternative Type "C" intraocular lens in accordance with the present invention with first and second optic elements.

3. Type "C" intraocular lens. Referring now to FIG. 13, an alternative embodiment of intraocular lens system 300 corresponding to the invention is shown that provides alternative means for adjustment of optical power. In this embodiment, the central optic portion 310 is coupled to any suitable haptics that further couple together an anterior lens element 322a and a posterior lens element 322b. Each of the lens elements 322a and 322b are shown in exemplary bi-convex shapes for convenience, but it should be appreciated that each element can be bi-convex, plano-convex, convexo-concave, or plano-concave to cooperate with the other as a compound lens when their spaced apart dimension (indicated at d) is altered relative to optical axis 325. This lens type is thus adapted for post-implantation power adjustment by altering the distance between lens elements. In contrast, the Type "A" embodiment was adapted for post-implantation power adjustment principally by changing the curvature of at least one surface of the lens. The elements of the Type "B" body can again be of a silicone polymeric material, an acrylic polymeric material, a hydrogel polymeric material or the like, or of PMMA. The lens body 310 again could be rolled or folded for introduction through a small diameter introducer.

As shown in FIG. 13, the peripheral body portion 350 that is outward of the central optic 310 has a first interior chamber portion 355A at each side of the lens that carries a selected charge-responsive fluid media M as described previously. The implant carries another cooperating second interior chamber portion similar to chamber 155B of FIG. 2 elsewhere in the peripheral body portion 350 that communicates with the first interior chamber portion 355A. The lens again carries a microporous structure that is intermediate the first and second chamber portions, 355A and 355B. The flow of fluid media M can be caused between the cooperating chamber portions 355A and 355B as described above. In FIG. 13, it can be seen that first bi-lateral chamber 355A in a repose condition is flattened or oval and is surrounded by a body wall 356 of resilient material that provides the repose shape. When chamber 355A is filled with additional fluid, its shape will distend so that the chamber is more round in cross-section to accommodate the additional volume. Thus, the dimension of chamber 355A and body wall 356 about the chamber will resiliently flex and increase in a dimension (from d to d') that is parallel to axis 325 thus providing a mechanism for moving the first and second lens elements 322a and 322b relative to one another. By this means, the power of the lens can be adjusted.

In another embodiment, the IOL of the invention can be simplified by having an interior chamber arrangement with a remote energy source and charge-responsive fluid media M (not shown) that is adapted to cause fluid flow in a single direction, for example, to cause fluid flow into a central optic chamber to increase lens power. Then, the IOL lens power would be implanted with the intention of increasing power post-implantation. In the event that power needed to be decreased, a needle could be inserted to remove fluid.

In another embodiment, the fluid media M in a chamber arrangement of the IOL can carry nanoparticles that are directly responsive to electromagnetic radiation to thereby heat up and expand the fluid. The fluid in one chamber could be selectively heated (e.g., by a optical radiation in the wavelength range of 380 nm to 2000 nm that excites nanoscale chromophore particles or resistively heated elements in or about fluid media M in response to the radiation) wherein the expanded fluid causes fluid flows through a one-way valve within the IOL chamber arrangement to alter the lens shape. Numerous types of one way valves are known in the art and fall within the scope of the invention.

Those skilled in the art will appreciate that the exemplary systems, combinations and descriptions are merely illustrative of the invention as a whole, and that variations in the dimensions and compositions of invention fall within the spirit and scope of the invention. Specific characteristics and features of the invention and its method are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. An intraocular lens, comprising:
an optic portion comprising a deformable anterior element that has an anterior surface and a posterior surface comprising a projection that projects proximally from the posterior surface, and a posterior element that has an anterior surface comprising a projection that projects anteriorly from the anterior surface and a posterior surface, the anterior element posterior surface and the posterior element anterior surface at least partially defining an optic chamber, the deformable anterior element having a non-uniform thickness in a portion of the intraocular lens adapted to focus light onto the retina, the anterior element projection and the posterior element projection being in the portion of the intraocular lens adapted to focus light onto the retina, the deformable anterior element having a smooth outer surface throughout the portion adapted to focus light onto the retina; and a peripheral non-optic portion extending peripherally from the optic portion, the peripheral portion in fluid communication with the optic chamber, wherein the intraocular lens is sized and configured to be implanted within a human eye.

2. The intraocular lens of claim 1 wherein the deformable anterior element is thinner at an optical axis of the optic portion than at a periphery of the optic chamber.

3. The intraocular lens of claim 1 wherein the deformable anterior element is thicker at an optical axis of the optic portion than at a periphery of the optic chamber.

4. The intraocular lens of claim 1 wherein the anterior element is secured to the posterior element.

5. The intraocular lens of claim 1 wherein the anterior element is secured to the posterior element in the peripheral non-optic portion of the intraocular lens.

6. The intraocular lens of claim 1 further comprising an intermediate body with a plurality of apertures therethrough between the optic chamber and the peripheral portion adapted to allow fluid to flow from the optic chamber to the peripheral portion.

7. The intraocular lens of claim 1 further comprising a fluid disposed in the optic chamber and the peripheral portion, wherein the fluid has an index of refraction that is substantially matched with an index of refraction of the anterior element and an index of refraction of the posterior element.

8. The intraocular lens of claim 1 wherein the deformable anterior element has a convex outer surface from an optical axis of the optic portion to a periphery of the optic chamber.

9. The intraocular lens of claim 1 wherein the posterior element has a non-uniform thickness in the portion adapted to focus light onto the retina.

10. The intraocular lens of claim 1 wherein the outer surface of the deformable anterior element is a smooth curve throughout the portion adapted to focus light onto the retina.

11. The intraocular lens of claim 1 further comprising a plurality of linear fluid channels perpendicular to an optical axis of the optic portion, the plurality of linear fluid channels providing fluid communication between the peripheral portion and the optic chamber.

12. The intraocular lens of claim 11 further comprising an intermediate body that comprises the plurality of linear fluid channels therethrough between the optic chamber and the peripheral portion adapted to allow fluid to flow between the optic chamber and the peripheral portion.

13. An intraocular lens comprising:
an optic portion comprising a singular deformable anterior element that has an anterior surface and a posterior surface comprising a projection that projects proximally from the posterior surface, and a posterior element that has an anterior surface comprising a projection that projects anteriorly from the anterior surface and a posterior surface, the anterior element posterior surface and the posterior element anterior surface at least partially defining an optic chamber, the singular deformable anterior element having a non-uniform thickness in a portion of the intraocular lens adapted to focus light onto the retina, the anterior element projection and the posterior element projection being in the portion of the intraocular lens adapted to focus light onto the retina, the singular deformable anterior element having a smooth outer surface throughout the portion adapted to focus light onto the retina; and a peripheral non-optic portion extending peripherally from the optic portion, the peripheral portion in fluid communication with the optic chamber, wherein the intraocular lens is sized and configured to be implanted within a human eye.

14. The intraocular lens of claim 13 wherein the deformable anterior element is thinner at an optical axis of the optic portion than at a periphery of the optic chamber.

15. The intraocular lens of claim 13 wherein the deformable anterior element is thicker at an optical axis of the optic portion than at a periphery of the optic chamber.

16. The intraocular lens of claim 13 wherein the deformable anterior element is secured to the posterior element.

17. The intraocular lens of claim 13 wherein the anterior element is secured to the posterior element in the peripheral non-optic portion of the intraocular lens.

18. The intraocular lens of claim 13 further comprising an intermediate body with a plurality of apertures therethrough between the optic chamber and the peripheral portion adapted to allow fluid to flow between the optic chamber and the peripheral portion.

19. The intraocular lens of claim 13 further comprising a fluid disposed in the optic chamber and the peripheral portion, wherein the fluid has an index of refraction that is substantially matched with an index of refraction of the anterior element and an index of refraction of the posterior element.

20. The intraocular lens of claim 13 wherein the posterior element has a non-uniform thickness in the portion adapted to focus light onto the retina.

21. The intraocular lens of claim 13 wherein the outer surface is convex from an optical axis of the optic portion to a periphery of the optic chamber.

22. The intraocular lens of claim 13 wherein the outer surface of the deformable anterior element is a smooth curve throughout the portion adapted to focus light onto the retina.

23. The intraocular lens of claim 13 further comprising a plurality of linear fluid channels perpendicular to an optical axis of the optic portion, the plurality of linear fluid channels providing fluid communication between the peripheral portion and the optic chamber.

24. The intraocular lens of claim 23 further comprising an intermediate body that comprises the plurality of linear fluid channels therethrough between the optic chamber and the peripheral portion adapted to allow fluid to flow between the optic chamber and the peripheral portion.

* * * * *